United States Patent [19]

Schmiegel et al.

[11] Patent Number: 4,602,044

[45] Date of Patent: Jul. 22, 1986

[54] β-PHENETHANOLAMINE ANTIOBESITY AGENTS

[75] Inventors: Klaus K. Schmiegel; Walter N. Shaw, both of Indianapolis, Ind.

[73] Assignee: Eli Lilly and Company, Indianapolis, Ind.

[21] Appl. No.: 562,960

[22] Filed: Dec. 19, 1983

[51] Int. Cl.⁴ .......................................... A61K 31/205
[52] U.S. Cl. .................................. 514/653; 514/554; 564/162; 564/166; 564/271; 564/304; 564/363; 260/501.18; 260/501.19
[58] Field of Search ............... 564/363, 304; 424/316, 424/330; 260/501.18, 501.19; 514/554, 653

[56] References Cited

U.S. PATENT DOCUMENTS

| | | | |
|---|---|---|---|
| 4,329,358 | 5/1982 | Ainsworth et al. | 424/309 |
| 4,382,958 | 5/1983 | Duckworth | 424/330 |
| 4,391,826 | 7/1983 | Mills et al. | 424/324 |
| 4,396,627 | 8/1983 | Ainsworth et al. | 424/309 |

FOREIGN PATENT DOCUMENTS

| | | | |
|---|---|---|---|
| 68669 | 1/1983 | European Pat. Off. | 564/363 |
| 89154 | 9/1983 | European Pat. Off. | |

OTHER PUBLICATIONS

U.S. application Ser. No. 462,587 filed 1/31/83 entitled Growth Promotion.

*Primary Examiner*—Robert V. Hines
*Attorney, Agent, or Firm*—Charles W. Ashbrook; Arthur R. Whale

[57] ABSTRACT

β-Phenethanolamines are useful as antiobesity agents.

17 Claims, No Drawings

β-PHENETHANOLAMINE ANTIOBESITY AGENTS

BACKGROUND OF THE INVENTION

The chemistry and use of β-phenethanolamines has been extensively investigated. A number of these compounds have been reported to have beneficial cardiac activities; see U.S. Pat. No. 3,987,200. Such compounds also are known to have sympathomimetic activity, and have found utility as utero-relaxing agents; Van Dijk et al., *Recueil*, 92 1281 (1973). More recently, a group of β-phenethanolamines have been reported as possessing antihyperglycemic activity, and have been found effective in promoting the loss of weight in animals; see EPO 6735 published Jan. 9, 1980 and U.S. Pat. No. 4,391,826.

An object of this invention is to provide a group of novel substituted β-phenethanolamines that are useful as antiobesity agents.

SUMMARY OF THE INVENTION

This invention provides compounds having the formula

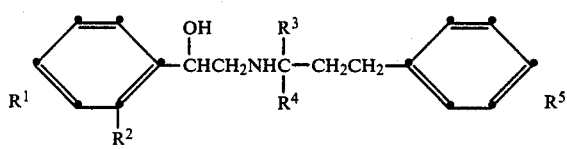

wherein:
R$^1$ is hydrogen or hydroxy;
R$^2$ is hydrogen or fluoro,
R$^3$ is hydrogen or C$_1$–C$_2$ alkyl;
R$^4$ is hydrogen or methyl;
R$^5$ is nitro or SO$_2$CH$_3$; and the pharmaceutically acceptable acid addition salts thereof.

Preferred compounds of the invention have the above formula wherein R$^1$, R$^2$ and R$^3$ are hydrogen, R$^4$ is methyl and R$^5$ is nitro, especially 4-nitro. The invention also provides pharmaceutical formulations comprising the compounds of the above formula, and a method of treating obesity in mammals employing the compounds.

DETAILED DESCRIPTION OF THE INVENTION

The compounds of this invention are readily prepared by reaction of a styrene oxide with a 3-phenylpropylamine derivative. For example, a styrene oxide such as 2-fluorostyrene oxide can be reacted with about an equimolar quantity of an amine such as 1-methyl-3-(4-nitrophenyl)propylamine in an unreactive organic solvent such as ethanol, methanol, n-propanol, dioxane, or the like. The reaction generally is carried out at a temperature of about 50° to about 120° C., and at such temperature the reaction routinely is substantially complete within about 6 to about 10 hours. The product, a β-phenethanolamine of the invention, is readily isolated by simply removing the reaction solvent, for instance by evaporation under reduced pressure, and further purification can be accomplished if desired by standard techniques, including crystallization, chromatography, acid-base extraction, and the like.

An alternative method for preparing the β-phenethanolamines of the above formula comprises reacting a mandelic acid derivative with a 3-phenylpropylamine derivative to provide an amide, which upon subsequent reduction provides a compound of the above formula. For example, a phenylpropylamine derivative such as 1-methyl-3-(3-methanesulfonylphenyl)propylamine can be reacted with an acylating agent such as a hydroxy protected mandelic acid halide, or preferably simply reacted with a mandelic acid in the presence of a common peptide coupling reagent such as N,N'-dicyclohexylcarbodiimide, carbonyldiimidazole or N-ethoxycarbonyl-2-ethoxy-1,2-dihydroquinoline, commonly referred to as EEDQ. The direct coupling reaction generally is conducted in an organic solvent such as benzene or N,N-dimethylformamide, and normally is complete after about 2 to 48 hours when carried out at about −30° to about 100° C. The product is an amide that is readily isolated by simply filtering the reaction mixture and then removing the reaction solvent. The amide thus formed is next reduced by reaction with a common reducing agent such as borane-dimethylsulfide complex or the like to provide a β-phenethanolamine defined by the above formula.

A similar, yet alternative, method of synthesis comprises reacting a phenethanolamine with a phenylethyl ketone to provide a Schiff base, which upon reduction gives a compound of the invention. For example, a phenethanolamine such as 2-hydroxy-2-(4-hydroxyphenyl)ethylamine can be reacted with a ketone such as methyl 2-(4-nitrophenyl)ethyl ketone to provide the corresponding imine, which upon reduction, for instance with sodium borohydride or the like, provides 1-(4-hydroxyphenyl)-2-[1-methyl-3-(4-nitrophenyl)propylamino]ethanol.

It should be noted that the compounds of this invention possess at least one asymmetric center (i.e. the carbinol center), and when R$^3$ and R$^4$ differ, the compounds possess two asymmetric centers. The R and S designation of absolute stereochemical configuration will be employed herein when naming specific optical isomers. When two asymmetric centers are present, at least two letters will be required to designate configuration. The first letter will designate the configuration at the phenethanol carbinol asymmetric center, and the second letter will designate the configuration at the asymmetric carbon bearing R$^3$ and R$^4$. For example, the compound of the above formula wherein R$^1$, R$^2$ and R$^3$ are hydrogen, R$^4$ is methyl, R$^5$ is 4-nitro, the phenethanol carbinol center is the R absolute configuration and the

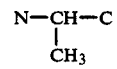

asymmetric center is the S configuration will be named: R,S-1-phenyl-2-[1-methyl-3-(4-nitrophenyl)propylamino]ethanol. No designation of optical configuration will of course infer a mixture of the possible isomers.

Since employment of individual optical isomers in the antiobesity method of this invention necessitates preparing the β-phenethanolamines from optically active starting materials, or using costly separation procedures, a preferred embodiment of the invention employs a mixture of optical isomers. For example 1-phenyl-2-[1-methyl-3-(4-nitrophenyl)propylamino]ethanol is preferably prepared from racemic mixtures of starting materials, e.g. dl-1-methyl-3-(4-nitrophenyl)propylamine and dl-styrene oxide, to provide a mixture of all four possible optical isomers of the product. The mixture of optical isomers preferably is subjected to separation procedures to remove the R,R-optical isomer, which appears to possess most or all of the adverse cardiotonic activity.

U.S. Pat. No. 4,391,826 teaches that only specific optical isomers of certain β-phenethanolamines can be employed to treat obesity, since some optical isomers are potent ionotropic agents and would cause adverse side effects if employed in an anti-obesity method. The reference specifically teaches that the R,R-optical isomers are cardiotonic and must be separated from the remaining isomers. We have now discovered that both the R,R and the R,S-isomers of the above formula are potent anti-obesity agents. As noted previously, the R,S-isomers are much less cardiotonic than the R,R-isomers. We have now found that either the S,R or the S,S isomer, or both, appear to antagonize cardiotonic effects, and use of a mixture of isomers therefore results in a further reduction in cardiotonic effects. Therefore, a preferred embodiment of the invention is a mixture of the R,S-isomer and the S,R and/or the S,S-isomer. In a preferred aspect of the invention, substantially all of the R,R optical isomers should be removed from a mixture to be employed in the anti-obesity method. It is contemplated that any mixture of isomers will comprise less than about ten percent by weight of any R,R optical isomer.

Since the β-phenethanolamines of this invention are inherently basic by virtue of a secondary amino group, they readily form pharmaceutically acceptable acid addition salts by reaction with any number of inorganic and organic acids. These salts often are preferred to the free base since they generally are more soluble in solvents such as water and are more conveniently formulated for pharmaceutical use. Acids commonly employed to form acid addition salts include mineral acids such as hydrochloric acid, sulfuric acid, phosphoric acid, perchloric acid and the like; and organic acids such as acetic acid, citric acid, succinic acid, para-toluene sulfonic acid, methanesulfonic acid, lactic acid and the like. Preferred salts to be employed in the present method include the hydrochlorides and hydrobromides.

Typical β-phenethanolamines provided by this invention include the following:

1-(3-hydroxyphenyl)-2-[1-methyl-1-ethyl-3-(4-nitrophenyl)propylamino]ethanol;
1-(2-fluoro-4-hydroxyphenyl)-2-[1-methyl-3-(4-nitrophenyl)propylamino]ethanol;
1-(4-hydroxyphenyl)-2-[3-(3-nitrophenyl)propylamino]ethanol;
1-(3-hydroxy-2-fluorophenyl)-2-[3-(4-methylsulfonyl)propylamino]ethanol;
R,S-1-phenyl-2-[1-methyl-3-(4-nitrophenyl)propylamino]ethanol;
S-1-phenyl-2-[1,1-dimethyl-3-(3-methylsulfonylphenyl)propylamino]ethanol;
R-1-(4-hydroxyphenyl)-2-[1,1-dimethyl-3-(4-nitrophenyl)propylamino]ethanol hydrochloride;
S,S-1-phenyl-2-[1-methyl-3-(4-nitrophenyl)propylamino]ethanol;
1-(3-hydroxyphenyl)-2-[1-methyl-3-(4-nitrophenyl)propylamino]ethanol succinate;
R-1-(4-hydroxyphenyl)-2-[1-methyl-1-ethyl-3-(4-nitrophenyl)propylamino]ethanol;
R-1-(4-hydroxyphenyl)-2-[1,1-dimethyl-3-(4-nitrophenyl)propylamino]ethanol hydrobromide; and
R-1-(4-hydroxyphenyl)-2-[1,1-dimethyl-3-(4-phenyl)propylamino]ethanol.

Because of the surprisingly low inotropic activity of the phenethanolamines of this invention, particularly when a mixture of R,S plus S,R and/or S,S isomers are employed, they can be administered to an animal at doses large enough to effect release of free fatty acids from adipose stores without causing a substantial increase in the pumping force of the heart. Such unique biological spectrum of the compounds of this invention renders them particularly useful in the control of weight in obese animals. As used herein, "weight control in obese animals" refers to the ability of the compounds of this invention to effect an actual weight reduction when administered to a mature obese animal, such as a human, whereas such compounds are effective in the prevention of excessive weight gain when administered to obese animals that are still in growing and developing stages of life. The terms "mature" and "immature" are used herein to refer to the generally accepted definitions of age and growth patterns. "Obesity" is an art recognized term and is used as such herein.

An additional aspect of this invention is a method for controlling weight in obese animals. While the anti-obesity effective dose of a compound of this invention employed in the control of obesity will vary depending on the particular agent employed and the severity of the condition being treated, the usual dosage of a compound of this invention will be from about 1.0 to about 50 mg. per kilogram of animal body weight. The compounds of the invention preferably will be administered orally at a dosage of from about 1 to about 25 mg./kg., generally given in individual doses from one to four times per day. When desired, the compound can be administered orally in the form of a tablet or capsule, or alternatively in sustained release form. According to the method of this invention a compound defined by the above general formula is administered to a mature obese animal to effect an actual reduction in weight without diminishing the daily food consumption. The compound will be administered daily, at increasing dosage levels if desired, until the desired weight reduction is effected. The compounds of the invention can be administered to an immature obese animal to effect a reduction in weight gain without a diminished daily food consumption. Once the immature obese animal reaches the age when structural growth ceases, a reduction of weight will be effected until a substantially normal weight is achieved.

The phenethanolamines comprehended by this invention can be formulated by normal procedures for convenient administration by any of a number of routes. It is preferred that the compounds be formulated for oral administration. Pharmaceutical formulations which are useful in weight control in obese animals are provided in a further embodiment of this invention.

Such pharmaceutical compositions can contain, as active ingredient, one or more of the compounds provided by this invention, preferably a combination of optical isomers as hereinbefore indicated, in addition to any of a number of pharmaceutically acceptable carriers or diluents. Typical carriers and diluents commonly used include gelatin, starch, dextrose, sucrose, lactose, cellulose derivatives, stearates, polyvinylpyrrolidine, glycerine, ethyl lactate, sorbitol, mannitol, and the like. A suitable pharmaceutical composition can additionally include any of a number of common preserving agents, stabilizers, antioxidants, taste correctors, and the like.

Examples of such additives include ascorbic acid, sorbic acid, various esters of p-hydroxybenzoic acid, and the like.

Typical pharmaceutical compositions useful in the treatment of obesity according to this invention will generally include from about 1 to about 95 percent by weight of a compound of this invention as active ingredient, and more normally about 20 to about 50 percent by weight. The remainder of said pharmaceutical composition will comprise suitable carriers and diluents.

A pharmaceutical composition containing as active ingredient at least one of the compounds of this invention can be molded into tablets, encapsulated into empty gelatin capsules, or made into a solution or suspension. Such pharmaceutical compositions can be administered to an obese subject in need of treatment by any of a number of routes, including the oral and parenteral routes. A preferred formulation, for example, comprises about 250 mg. of R,S and S,R-N-1-phenyl-2-[1-methyl-3-(4-nitrophenyl)propylamino]ethanol hydrochloride admixed with any of a number of suitable carriers and molded into a tablet for oral administration to an obese human subject at the rate of from 1 to about 4 tablets per day for effective weight control.

In an effort to more fully illustrate particular aspects of this invention, the following detailed examples of the preparation of starting materials and the final products of this invention are provided. The examples are representative only and should not be construed as limiting in any respect.

EXAMPLE 1

1-Phenyl-2-[1-methyl-3-(4-nitrophenyl)-propylamino]ethanol

A solution of 5.0 g. (25.9 mM) of 2-amino-1-phenylethanol and 3.55 g. (25.9 mM) of methyl 2-(4-nitrophenyl)ethyl ketone in 60 ml. of toluene containing 10 mg. of para-toluenesulfonic acid was heated at reflux for six hours in a flask equipped with a Dean-Stark trap. The water that formed during the reaction was removed via the trap, and then the reaction mixture was cooled to room temperature and concentrated to dryness by evaporation of the solvent under reduced pressure. The solid product that remained was dissolved in 50 ml. of tetrahydrofuran and the solution was heated to reflux. A solution of 13.5 ml. of 2N borane-methyl sulfide complex in tetrahydrofuran was then added dropwise to the reaction mixture, and the mixture was refluxed for an additional ninety minutes. After cooling the reaction mixture to room temperature, it was diluted by addition of diethyl ether saturated with hydrogen chloride. The precipitate that formed was collected by filtration and crystallized from ethanol and diethyl ether to give 3.29 g. of a racemic diastereomeric mixture of 1-phenyl-2-[1-methyl-3-(4-nitrophenyl)-propylamino]ethanol hydrochloride. M.P. 203°–213° C.

Analysis calc. for $C_{18}H_{23}ClN_2O_3$: Theory: C, 61.62; H, 6.61; N, 7.98; Cl, 10.11. Found: C, 61.76; H, 6.62; N, 7.76; Cl, 10.13.

EXAMPLE 2

(R,S)(S,R)-1-Phenyl-2-[1-methyl-3-(4-nitrophenyl)-propylamino]ethanol, hydrochloride The procedure of Example 1 was repeated except that the free base obtained from the borane-methyl sulfide reduction was not converted to the hydrochloride salt but, instead, was subjected to multiple recrystallizations from acetonitrile, benzene, isopropyl alcohol (in that order) to give the free base as the racemic (R,S) (S,R)-diastereomer.

The diastereomer was then converted to the hydrochloride salt by dissolving it in methanol and adding a solution of ethereal hydrogen chloride. (R,S)(S,R)-1-Phenyl-2-[1-methyl-3-(4-nitrophenyl)propylamino]ethanol hydrochloride was collected by filtration and air dried and exhibited a melting point of 198° to 202° C.

EXAMPLE 3

1-Phenyl-2-[1-methyl-3-(4-methylsulfonylphenyl)-propylamino]ethanol hydrochloride Methyl 2-(4-methylthiophenyl)ethyl ketone was oxidized by reaction with m-chloroperbenzoic acid to give methyl 2-(4-methylsulfonylphenyl)ethyl ketone. A solution of 6.73 g. of 2-amino-1-phenylethanol and 11.10 g. of methyl 2-(4-methylsulfonylphenyl)ethyl ketone in 500 ml. of toluene containing 200 mg. of p-toluenesulfonic acid was heated at reflux for twenty-four hours. The reaction mixture was cooled and the solvent was removed by evaporation to give the Schiff base 1-phenyl-2-[1-methyl-3-(4-methylsulfonylphenyl)-propylimino]ethanol. The Schiff base thus prepared was reacted with 3.7 g. of sodium borohydride in 500 ml. of ethanol at 0° C. for sixteen hours. The reaction mixture was diluted by addition of 50 ml. of acetone and 20 ml. of 3N hydrochloric acid. The mixture was concentrated to an oil by evaporation of the solvent. The oil crystallized upon standing at room temperature. Recrystallization of the product from 200 ml. of hot ethanol afforded 8.96 g. (48% yield) of 1-phenyl-2-[1-methyl-3-(4-methylsulfonylphenyl)propylamino]ethanol hydrochloride. M.P. 164°–170° C.

Analysis calc. for $C_{19}H_{26}ClNO_3S$: Theory: C, 59.44; H, 6.83; N, 3.65; Cl, 9.23; S, 8.35. Found: C, 59.28; H, 6.57; N, 3.70; Cl, 9.36; S, 8.11.

EXAMPLE 4

Preparation of Tablets

R,S-1-Phenyl-2-[1-methyl-3-(4-nitrophenyl)-propylamino]ethanol hydrochloride: 120 mg.
S,R-1-Phenyl-2-[1-methyl-3-(4-nitrophenyl)-propylamino]ethanol hydrochloride: 120 mg.
Lactose: 200 mg.
Corn Starch: 300 mg.
Corn Starch Paste: 50 mg.
Calcium Stearate: 5 mg.
Dicalcium Phosphate: 45 mg.

The active agents (prepared as described in Example 2), corn starch, lactose, and dicalcium phosphate are uniformly blended. The corn starch paste is prepared as a 10 percent aqueous paste and is blended into the mixture to uniformity. The mixture is blended with the calcium stearate and then compressed into tablets. Such tablets can be administered to an obese subject at the rate of 1 to about 4 tablets per day or as needed.

EXAMPLE 5

Preparation for Suppositories

R,S-1-Phenyl-2-[1-methyl-3-(4-methylsulfonylphenyl)-propylamino]ethanol hydrochloride: 500 mg.
Theobroma oil: 1500 mg.

The above ingredients are blended to uniformity at a temperature of about 60° C. and then permitted to cool in a tapered mold. Each suppository will weight about 2 grams and can be administered to a mature obese subject from 1 to 2 times each day for the reduction of

EXAMPLE 6

Preparation for Oral Suspension

R,S-1-(2-fluorophenyl)-2-[1-methyl-3-(4-nitrophenyl)-propylamino]ethanol hydrogen acetate: 5000 mg.
Sorbitol solution (70% N.F.): 40 ml.
Sodium benzoate: 150 mg.
Lactose: 10 mg.
Cherry flavor: 50 mg.
Distilled water q.s. ad: 100 ml.

The sorbitol solution is added to 40 ml. of distilled water and the R,S-N-1-(2-fluorophenyl)-2-[1-methyl-3-(4-nitrophenyl)propylamino]ethanol hydrogen acetate is dissolved therein. The lactose, sodium benzoate and flavoring are added and dissolved. The volume of the solution is adjusted to 100 ml. with distilled water. Each ml. of syrup contains 50 mg. of active drug. A mature obese mammal will be administered about 5 to about 20 ml. of syrup each day for the effective loss of weight.

The compounds provided by this invention are useful as anti-obesity agents. This utility has been demonstrated in laboratory tests designed to establish anti-obesity activity. The following procedure was employed to demonstrate the anti-obesity activity of the claimed compounds.

Genetically obese Zucker rats were divided into two groups, one serving as the control and the other as experimental being treated with the invention compounds. Both groups were allowed food (Camm Research) and water ad libitum. The animals were housed one to a plastic cage (containing wood-chip bedding) in a room maintained between 72° and 75° F. and having controlled light (0700 to 1900) and dark (1900 to 0700) cycles. Every morning each obese rat was weighed before test compound or control medium was administered and the food consumption over the previous 24 hours measured. The control obese rats were given 0.25 ml of a solution of 10 percent DMSO in 0.9 percent saline (v/v) per 100 gm body weight per os twice daily during the light cycle. The experimental obese rats were given 0.25 ml of a 10 percent DMSO-saline solution (v/v) containing an invention compound per 100 gm body weight per os twice daily at 8:30 a.m. and 3:30 p.m.

The effect of a preferred invention compound, 1-phenyl-2-[1-methyl-3-(4-nitrophenyl)propylamino]ethanol, hydrochloride, (the compound of Example 1) was judged by the difference in the pattern of weight gain in the treated group when compared to that of the control group. In none of the three replicated experiments was the decreased body weight gain or lack of body weight gain associated with a decrease in food intake.

A comparison of the three studies is as follows:

|  | I | II | III |
| --- | --- | --- | --- |
| no. of rats per group | 6 | 6 | 5 |
| no. of females per group | 3 | 3 | 5 |
| no. of males per group | 3 | 3 | 0 |
| age range at start, days | 97–112 | 99–118 | 94–102 |
| dose of test compound, mg/kg., p.o. | 2.5 | 0.5–2.5 | 2.5 |
| duration of treatment, days | 38 | 55 | 42 |

TABLE I

| Compound of Example 1 mg/kg (p.o.) | Days of Treatment | Body Weight Change in grams* Control | Body Weight Change in grams* Treated |
| --- | --- | --- | --- |
| (I) | | | |
| 0 | 0 | 0 | 0 |
| 2.5 | 5 | +4.1 | −4.0 |
| 2.5 | 10 | +11.0 | −4.2 |
| 2.5 | 15 | +15.5 | −5.0 |
| 2.5 | 20 | +21.8 | +1.3 |
| 2.5 | 25 | +19.5 | −4.8 |
| 2.5 | 30 | +24.5 | −1.5 |
| 2.5 | 35 | +32.8 | −5.0 |
| 2.5 | 38 | +39.5 | −7.7 |
| (II) | | | |
| 0 | 0 | 0 | 0 |
| 2.5 | 7 | +14.8 | −3.0 |
| 2.5 | 16 | +31.0 | −6.5 |
| 1.0 | 7 | +43.5 | +9.6 |
| 1.0 | 14 | +50.0 | +11.8 |
| 1.0 | 21 | +58.7 | +17.8 |
| 1.0 | 26 | +62.5 | +19.3 |
| 0.5 | 8 | +70.0 | +34.3 |
| 1.5 | 6 | +70.8 | +29.8 |
| (III) | | | |
| 0 | 0 | 0 | 0 |
| 2.5 | 7 | +15.2 | +4.0 |
| 2.5 | 14 | +26.4 | +9.2 |
| 2.5 | 21 | +32.8 | +3.4 |
| 2.5 | 28 | +38.0 | −7.2 |
| 2.5 | 35 | +44.4 | −10.6 |
| 2.5 | 42 | +50.6 | −11.0 |

*Body weight change is the change from day 1 of treatment.

A similar study was carried out employing the mixture of R,S and S,R-optical isomers prepared in Example 2. In this study, obese Zucker rats that were 5–6 months old at the start of the study were used. The test groups were as follows:

|  | Control | Treated |
| --- | --- | --- |
| no. of rats per group | 10 | 9 |
| no. of females per group | 8 | 5 |
| no. of males per group | 2 | 4 |
| age at start, days | 148–185 | 168–185 |
| dose of test compound, mg/kg, p.o. b.i.d. | 0 | 2 and 4 |

The treated group was administered 2 mg/kg of the compound of Example 2 for the first 21 days of the study. For the next 21 days, each treated animal received 4 mg/kg of the Example 2 compound.

The results of the study for the 42 day period are given in Table II.

TABLE II

| Compound of Example 2 mg/kg | Days of Treatment | Body Weight Change in grams* Control | Body Weight Change in grams* Treated |
| --- | --- | --- | --- |
| 0 | 0 | 0 | 0 |
| 2 | 7 | +9.7 | +4.0 |
| 2 | 14 | +17.8 | +9.0 |
| 2 | 21 | +21.1 | +11.3 |
| 4 | 28 | +26.0 | +13.1 |
| 4 | 35 | +30.8 | +12.6 |
| 4 | 42 | +34.8 | +12.7 |

*Body Weight change is change from day 1 of treatment

The compound of Example 3 was evaluated in a similar study employing the following groups of obese Zucker rats.

|  | Control | Treated |
| --- | --- | --- |
| no. of rats per group | 4 | 6 |
| no. of females per group | 4 | 3 |
| no. of males per group | 0 | 3 |
| age at start, days | 118–131 | 118–131 |
| compound dose, mg/kg, p.o. b.i.d. | 0 | 18 and 36 |
| duration of treatment, days |  | 13 at 18 mg/kg |
|  |  | 16 at 36 mg/kg |

The results of the study are presented in Table III

TABLE III

| Compound of Example 3 | Days of | Body Weight Change in grams* | |
| --- | --- | --- | --- |
| mg/kg | Treatment | Control | Treated |
| 0 | 0 | 0 | 0 |
| 18 | 6 | +7.5 | +12.3 |
| 18 | 13 | +18.5 | +30.7 |
| 36 | 7 | +26.5 | +29.0 |
| 36 | 15 | +33.5 | +24.0 |

*Body weight change is change from day 1 of treatment

The foregoing data demonstrate that the compounds of this invention effect weight loss in obese animals or cause a reduction in the rate of gain with normal feed intake. The compounds of the invention are potentially of value in the treatment of obesity in humans, particularly in view of their diminished cardiac effects. As noted above, it is believed that this ability may be most significant in connection with a mixture of the R,S and S,R enantiomers. As can be seen from the above Table the para-nitro compound is a preferred embodiment since it is a very potent anti-obesity agent. It also is orally active and can therefore be administered in the form of orally-acceptable pharmaceutical formulations such as tablets or capsules.

We claim:

1. A compound of the formula

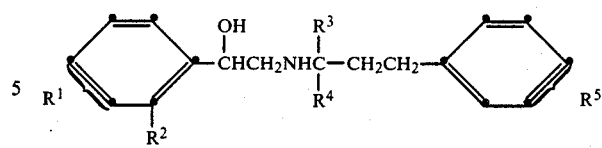

wherein:

$R^1$ is hydrogen or hydroxy;
$R^2$ is hydrogen or fluoro;
$R^3$ is hydrogen or $C_1$–$C_2$ alkyl;
$R^4$ is hydrogen or methyl;
$R^5$ is nitro or $SO_2CH_3$; and the pharmaceutically acceptable acid addition salts thereof.

2. The compound of claim 1 wherein $R^1$ is hydrogen.
3. The compound of claim 2 wherein $R^2$ is hydrogen.
4. The compound of claim 3 wherein $R^3$ is hydrogen.
5. The compound of claim 4 wherein $R^4$ is methyl.
6. The compound of claim 5 wherein $R^5$ is nitro.
7. The compound of claim 6 wherein $R^5$ is 4-nitro.
8. The compound of claim 7 which is comprised of the R,S and S,R optical isomers.
9. A pharmaceutical formulation comprising a compound of claim 1 admixed with a pharmaceutically acceptable diluent, carrier or excipient therefor.
10. The formulation of claim 9 employing a compound wherein $R^1$ is hydrogen.
11. The formulation of claim 10 employing a compound wherein $R^2$ is hydrogen.
12. The formulation of claim 11 employing a compound wherein $R^3$ is hydrogen.
13. The formulation of claim 12 employing a compound wherein $R^4$ is methyl.
14. The formulation of claim 13 employing a compound wherein $R^5$ is 4-nitro.
15. A method for effecting weight reduction in an obese subject comprising administering an anti-obesity effective amount of a compound of claim 1.
16. The method of claim 15 employing a compound wherein $R^1$, $R^2$ and $R^3$ are hydrogen.
17. The method of claim 6 employing a compound wherein $R^5$ is 4-nitro.

* * * * *